US00PP31577P2

(12) United States Plant Patent
Olesen

(10) Patent No.: US PP31,577 P2
(45) Date of Patent: Mar. 24, 2020

(54) COMPACT FLORIBUNDA ROSE PLANT NAMED 'POULPAL075'

(50) Latin Name: ***Rosa* hybrid**
Varietal Denomination: Poulpal075

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 15/999,583

(22) Filed: Sep. 4, 2018

(51) Int. Cl.
*A01H 5/02* (2018.01)
*A01H 6/74* (2018.01)

(52) U.S. Cl.
USPC ..... Plt./147
CPC ..... *A01H 6/749* (2018.05)

(58) Field of Classification Search
USPC ..... Plt./147
CPC ..... A01H 6/749; A01H 5/02
See application file for complete search history.

(56) References Cited

PUBLICATIONS

Poulsen Roser, Jun. 11, 2019.*

* cited by examiner

*Primary Examiner* — Keith O. Robinson

(57) ABSTRACT

A new garden rose plant of the Compact Floribunda class which has abundant, apricot flowers and attractive foliage. This new and distinct variety has shown to be uniform and stable in the resulting generations from asexual propagation.

1 Drawing Sheet

Botanical designation: *Rosa* hybrid.
Variety denomination: 'Poulpal075'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpal075', originated as a single seedling from the stated cross.

The new variety may be distinguished from its male pollen parent and female seed parent primarily by the following characteristics. The male pollen parent plant has yellow flowers while the new variety has apricot flowers. The female seed parent plant has orange red flowers while the new variety has apricot flowers.

The objective of the hybridization of this rose variety was to create a new and distinct variety with unique qualities, such as:

1. Uniform and abundant apricot flowers;
2. Vigorous, but compact growth when propagated on its own roots;
3. Exceptional disease resistance.

This combination of qualities is not present in previously available commercial cultivars of this type, known to the inventor, and distinguish 'Poulpal075' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpal075' was selected in the spring of 2008 by the inventor as a single plant from the progeny of the aforementioned hybridization.

Asexual reproduction of 'Poulpal075' by rooted cuttings was first done by Mogens N. Olesen in the nursery in Fredensborg, Denmark in July, 2008. This initial and other subsequent asexual propagations conducted in controlled environments have demonstrated that the characteristics of 'Poulpal075' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpal075'. Specifically illustrated the drawing are open flowers, petals detached, sepals detached, leaves, reproductive flower parts, stems, and a cluster of flowers attached to the branch. Plants shown are 2 years of age.

DETAILED DESCRIPTION OF THE VARIETY

The following is a description of 'Poulpal075', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpal049', U.S. Plant Pat. No. 24,224 are compared to 'Poulpal075' in Chart 1.

CHART 1

| | 'Poulpal075' | 'Poulpal049' |
|---|---|---|
| Petal Count | 35 | 35 |
| Flower Diameter | 85 mm | 80 mm |
| General Tonality of Flower Color | Orange Group 25C | Yellow-Orange Group 21D with intonations of Red Group 37A |

Flower and Flower Bud

Blooming habit: Continuous.

Flower bud:

*Size*.—Upon opening, 25 mm in length from base of receptacle to end of bud. Bud diameter is 13 mm.

*Bud form*.—Ovoid.

*Bud color*.—As sepals divide petals are Orange Group 29B and Orange Group 26A. Other intonations observed Orange-Red Group N34A.

*Sepal inner surface*.—Color: Yellow-Green Group 147C. Surface: Lightly pubescent.

*Sepal outer surface*.—Color: Yellow-Green Group 144A, with intonations of Greyed-Purple Group 183B. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—28 mm long, 10 mm wide.

*Receptacle*.—Texture: Smooth. Size: 7 mm in height, 10 mm wide. Color: Yellow-Green Group 144A. Shape: Campanulate.

*Pedicel*.—Surface: Smooth. Length: 30 mm. Diameter: 2 mm on average. Color: Yellow-Green Group 144B, with intonations of Greyed-Red Group 179B. Strength: Strong.

Flower bud development: Flower buds are borne in clusters of about 5 flower buds per stem. Development as a corymb.

Flower bloom:

*Fragrance*.—Mild floral rose like scent.

*Duration*.—The blooms have a duration on the plant of approximately 10 days. Petals fall cleanly away from plant after flowers have fully matured.

*Size*.—Flower diameter is 85 mm when open. Flower depth is 45 mm.

*Shape of flower, side view*.—The upper portion is flat. The lower portion is flat and concave.

Petalage: Double flower. Under normal conditions, flowers have about 35 petals.

General tonality of flower: Open flowers are Orange Group 25C.

Petal color:

*Upon opening, outer petals* .—Upper surface: Orange Group 25B, splashed with Orange Group 24C. At the basal zone, Yellow Group 14A. Lower surface: Yellow-Orange Group 16C, splashed with Orange Group 26B and Orange-Red Group 33C. Upon opening, inner petals: Upper surface: Orange Group N25A splashed with Yellow-Orange Group 14B. Yellow-Orange Group 14A at the petal base. Lower surface: Orange Group 29A splashed with Yellow-Orange Group 22B. Basal petal spots, upon opening: Upper surface: Yellow Group 14A. Lower surface: Yellow Group 12A. After opening, outer petals Upper surface: Yellow Group 12D, splashed with Orange Group 24D at margins. Yellow Group 12B at the petal base. Lower surface: Yellow Orange 14D, with marginal intonations of Orange Group 24D. After opening, inner petals: Upper surface: Yellow-Orange Group 22D, with intonations of Yellow-Orange Group 14C at middle zone. Yellow Group 13B at base. Lower surface: Yellow-Orange Group 22D, with marginal intonations of Orange Group 29D. At the base of the petal, Yellow Group 13C. Basal petal spots, after opening: Upper surface: Yellow Group 13B, about 6 to 8 mm in length. Lower surface: Yellow Group 13C, about 6 to 8 mm in length.

Petals:

*Petal reflex*.—None.

*Margin*.—Entire and uniform. No undulations.

*Shape*.—Rounded. Apex shape: Rounded. Base shape: Rounded.

*Size*.—50 mm (l)×53 mm (w).

*Texture*.—Smooth.

*Thickness*.—Average.

Petaloids:

*Size*.—40 mm (l) by 30 mm (w).

*Quantity*.—About 6.

*Shape*.—Elliptical with an acute base and rounded apices.

*Color*.—On the upper surface, Yellow-Orange Group 22D, with intonations of Yellow-Orange Group 14C and Yellow Group 13B at base. The underside is Yellow-Orange Group 22D, with marginal intonations of Orange Group 29D and Yellow Group 13C at the base.

Reproductive flower parts:

*Pollen*.—None observed.

*Anthers*.—Size: 2 mm in length. Color: Yellow Group 8A. Quantity: 38 on average.

*Filaments*.—Color: Yellow Group 13A. Length: 4 mm.

*Pistils*.—Length: 8 mm. Quantity: 25 on average.

*Stigmas*.—Color: Greyed-Yellow Group 160B.

*Styles*.—Color: Red Group 43C. Hips: None Observed.

Plant

Plant growth: Upright, bushy. Plants are 40 cm in height, and 37 cm wide.

Stems:

*Color of juvenile growth*.—Yellow-Green Group 146D, with intonations of Greyed-Purple Group 183A.

*Color of mature growth*.—Yellow-Green Group 146C.

*Length*.—Canes are about 17 cm from the base of the plant to the flowering portion.

*Diameter*.—About 5 mm.

*Internodes*.—On mature canes about 42 mm between nodes.

*Surface texture*.—Young wood: Smooth. Older wood: Smooth.

Long prickles: None observed.

Plant foliage:

*Compound leaf*.—130 mm (l)×115 (w).

*Quantity*.—2 leaves per 10 cm of stem on average.

*Leaf bearing angle to the stem*.—45 degrees.

*Color of juvenile foliage*.—Upper and lower side: Yellow-Green Group 146A, with strong intonations of Greyed-Purple Group 183A.

*Color of mature foliage*.—Upper side: Yellow-Green Group 147A. Lower side: Yellow-Green Group 147B.

Plant leaves and leaflets:

*Stipules*.—Size: 12 mm long, 4 mm wide. Quantity: 2 per compound leaf. Shape: Linear, slightly broad based with outward extending apices. Margins: Finely serrated. Color: Yellow-Green Group 144B.

*Petiole*.—Length: 30 mm. Diameter: 2 mm. Upper surface color: Yellow-Green Group 144B. Lower surface color: Yellow-Green Group 144B.

*Rachis*.—Length: 40 mm. Upper surface color: Yellow-Green Group 144B. Lower surface color: Yellow-Green Group 144B.

*Leaflet*.—Quantity: Normally 7 leaflets. Margins: Serrated. Size: Terminal leaflets are about 60 mm long, 38 mm wide. Shape: Generally elliptical. Base: Rounded. Apex: Acute. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal075', substantially as illustrated and described herein, due to its abundant apricot flowers, disease resistance, and extended period of bloom.

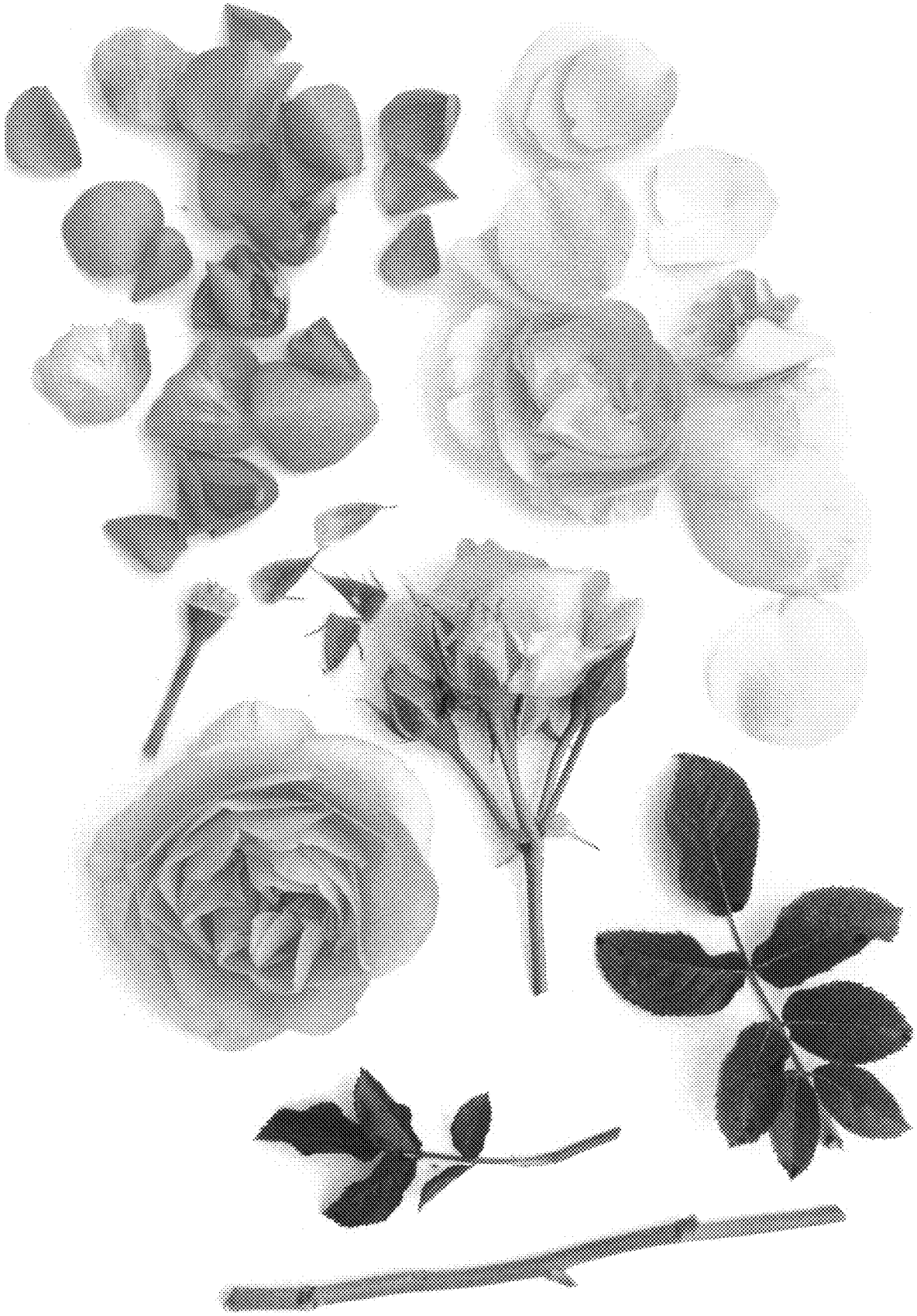

* * * * *